United States Patent
Drouet et al.

(10) Patent No.: US 9,696,308 B2
(45) Date of Patent: Jul. 4, 2017

(54) USE OF AT LEAST ONE BIOMARKER FOR THE IN VITRO PROGNOSIS OR DIAGNOSIS OF LYMPHOPROLIFERATIVE EPISODES ASSOCIATED WITH THE EPSTEIN-BARR VIRUS (EBV)

(71) Applicant: UNIVERSITE JOSEPH FOURIER, Grenoble (FR)

(72) Inventors: Emmanuel Drouet, Corenc (FR); Mohammed Habib, Saint Etienne (FR); Felix Agbalika, Paris (FR)

(73) Assignee: UNIVERSITE JOSEPH FOURIER, Grenoble (FR)

( * ) Notice: Subject to any disclaimer, the term of this patent is extended or adjusted under 35 U.S.C. 154(b) by 0 days.

(21) Appl. No.: 14/363,050

(22) PCT Filed: Dec. 4, 2012

(86) PCT No.: PCT/FR2012/052790
§ 371 (c)(1),
(2) Date: Jul. 1, 2014

(87) PCT Pub. No.: WO2013/083906
PCT Pub. Date: Jun. 13, 2013

(65) Prior Publication Data
US 2014/0342349 A1     Nov. 20, 2014

(30) Foreign Application Priority Data
Dec. 5, 2011 (FR) ...................................... 11 61167

(51) Int. Cl.
| | | |
|---|---|---|
| C07K 14/005 | (2006.01) | |
| C12N 7/00 | (2006.01) | |
| G01N 33/569 | (2006.01) | |
| C07K 16/08 | (2006.01) | |
| C12Q 1/70 | (2006.01) | |

(52) U.S. Cl.
CPC ..... *G01N 33/56994* (2013.01); *C07K 14/005* (2013.01); *C07K 16/085* (2013.01); *C12N 7/00* (2013.01); *C12Q 1/705* (2013.01); *C12N 2710/16222* (2013.01); *C12N 2710/16231* (2013.01); *C12Q 2600/118* (2013.01)

(58) Field of Classification Search
CPC .............. A61K 2039/525; C12Q 1/705; C12Q 2600/118; C12N 15/113; C12N 15/1133; C07K 16/085; G01N 33/56994
See application file for complete search history.

(56) References Cited

U.S. PATENT DOCUMENTS

2004/0214161 A1   10/2004   Smith

FOREIGN PATENT DOCUMENTS

| FR | WO9621155 | * | 7/1996 |
|---|---|---|---|
| WO | 9621155 A1 | | 7/1996 |
| WO | 2009112497 A1 | | 9/2009 |

OTHER PUBLICATIONS

Imbert-Marcille et al. Clinical and Diagnostic Laboratory Immunology (2000), 7(2), 206-211.*
Biggin M et al. J. Virol. 1987, vol. 61 (10), pp. 3120-3132.*
Dardari et al. Journal Clinical Virology, 2008, vol. 41, pp. 96-103.*
Dardari et al., "Analyses of the prognostic significance of the Epstein-Barr virus transactivator ZEBRA protein and diagnostic value of its two synthetic peptides in nasopharyngeal carcinoma", Journal of Clinical Virology, 2008, vol. 41, pp. 96-103.
Hilscher et al., "Faster quantitative real-time PCR protocols may lose sensitivity and show increased variability", Nucleic Acids Research, 2005, vol. 33, No. 21, e182, pp. 1-8.
Katz et al., "Viral proteins associated with the Epstein-Barr virus transactivator, ZEBRA", Proc. Natl. Acad. Sci. USA, 1992, vol. 89, pp. 378-382.
Tabaa et al., "Functional Epstein-Barr virus reservoir in plasma cells derived from infected peripheral blood memory B cells", Blood, 2009, vol. 113, No. 3, pp. 603-611.
Tan et al., "Quantification of Epstein-Barr virus DNA load, interleukin-6, interleukin-10, transforming growth factor-$\beta 1$ and stem cell factor in plasma of patients with nasopharyngeal carcinoma", BMC Cancer, 2006, vol. 6, p. 227, XP021016225.
Tardif et al., "Impaired Protein Kinase C Activation/Translocation in Epstein-Barr Virus-infected Monocytes", The Journal of Biological Chemistry, 2002, vol. 277, pp. 24148-24154.
Wadowsky et al., "Measurement of Epstein-Barr Virus DNA Loads in Whole Blood and Plasma by TaqMan PCR and in Peripheral Blood Lymphocytes by Competitive PCR", Journal of Clinical Microbiology, 2003, vol. 41, No. 11, pp. 5245-5249.
Young et al., "Differentiation-Associated Expression of the Epstein-Barr Virus BZLF1 Transactivator Protein in Oral Hairy Leukoplakia", 1991, vol. 65, No. 6, pp. 2868-2874.
International Search Report, dated Mar. 21, 2013, from corresponding PCT application.

* cited by examiner

*Primary Examiner* — Bao Li
(74) *Attorney, Agent, or Firm* — Young & Thompson

(57) ABSTRACT

A protein complex isolated from its natural medium and including the ZEBRA protein of sequence SEQ ID NO: 1, the isolated protein complex having the following properties:
- it is more stable than the ZEBRA protein, in particular it is more resistant to the action of the proteases than the ZEBRA protein,
- it is capable of specifically binding the AZ125 and AZ130 monoclonal antibodies,
- it is soluble in a body fluid, and in particular a body fluid selected from the group constituted by blood and serum, and to its detection process and the uses of this process for the prognosis or diagnosis of lymphoproliferative episodes associated with the EBV.

8 Claims, 1 Drawing Sheet

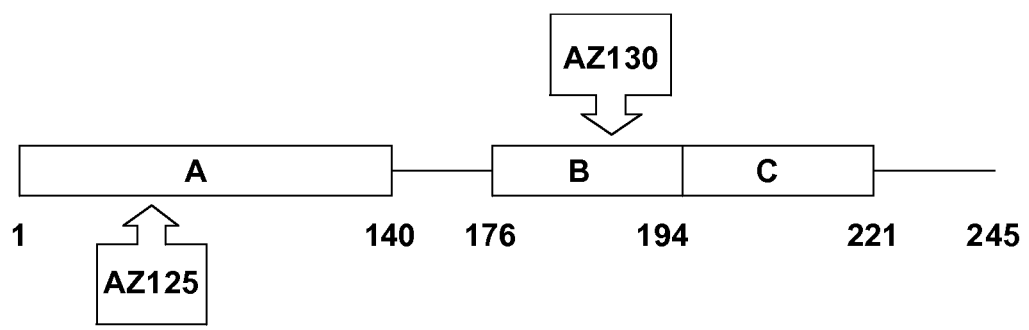

SEQUENCE LISTING

<160> NUMBER OF SEQ ID NOS: 8

<210> SEQ ID NO 1
<211> LENGTH: 245
<212> TYPE: PRT
<213> ORGANISM: Epstein-Barr virus

<400> SEQUENCE: 1

```
Met Met Asp Pro Asn Ser Thr Ser Glu Asp Val Lys Phe Thr Pro Asp
1               5                   10                  15

Pro Tyr Gln Val Pro Phe Val Gln Ala Phe Asp Gln Ala Thr Arg Val
            20                  25                  30

Tyr Gln Asp Leu Gly Gly Pro Ser Gln Ala Pro Leu Pro Cys Val Leu
        35                  40                  45

Trp Pro Val Leu Pro Glu Pro Leu Pro Gln Gly Gln Leu Thr Ala Tyr
    50                  55                  60

His Val Ser Thr Ala Pro Thr Gly Ser Trp Phe Ser Ala Pro Gln Pro
65                  70                  75                  80

Ala Pro Glu Asn Ala Tyr Gln Ala Tyr Ala Ala Pro Gln Leu Phe Pro
                85                  90                  95

Val Ser Asp Ile Thr Gln Asn Gln Gln Thr Asn Gln Ala Gly Gly Glu
            100                 105                 110

Ala Pro Gln Pro Gly Asp Asn Ser Thr Val Gln Thr Ala Ala Ala Val
        115                 120                 125

Val Phe Ala Cys Pro Gly Ala Asn Gln Gly Gln Gln Leu Ala Asp Ile
    130                 135                 140

Gly Val Pro Gln Pro Ala Pro Val Ala Ala Pro Ala Arg Arg Thr Arg
145                 150                 155                 160

Lys Pro Gln Gln Pro Glu Ser Leu Glu Glu Cys Asp Ser Glu Leu Glu
                165                 170                 175

Ile Lys Arg Tyr Lys Asn Arg Val Ala Ser Arg Lys Cys Arg Ala Lys
            180                 185                 190

Phe Lys Gln Leu Leu Gln His Tyr Arg Glu Val Ala Ala Ala Lys Ser
        195                 200                 205

Ser Glu Asn Asp Arg Leu Arg Leu Leu Leu Lys Gln Met Cys Pro Ser
    210                 215                 220

Leu Asp Val Asp Ser Ile Ile Arg Arg Thr Pro Asp Val Leu His Glu
```

Asp Leu Leu Asn Phe
         245

<210> SEQ ID NO 2
<211> LENGTH: 19
<212> TYPE: DNA
<213> ORGANISM: Artificial Sequence
<220> FEATURE:
<223> OTHER INFORMATION: BALF-5_F

<400> SEQUENCE: 2
cggaagccct ctggacttc                                            19

<210> SEQ ID NO 3
<211> LENGTH: 21
<212> TYPE: DNA
<213> ORGANISM: Artificial Sequence
<220> FEATURE:
<223> OTHER INFORMATION: BALF-5_R

<400> SEQUENCE: 3
ccctgtttat ccgatggaat g                                         21

<210> SEQ ID NO 4
<211> LENGTH: 23
<212> TYPE: DNA
<213> ORGANISM: Artificial Sequence
<220> FEATURE:
<223> OTHER INFORMATION: BALF-5_P

<400> SEQUENCE: 4
tgtacacgca cgagaaatgc gcc                                       23

<210> SEQ ID NO 5
<211> LENGTH: 18
<212> TYPE: DNA
<213> ORGANISM: Artificial Sequence
<220> FEATURE:
<223> OTHER INFORMATION: ZEBRA_F

<400> SEQUENCE: 5
ccaggcttgg gcacatct                                             18

<210> SEQ ID NO 6
<211> LENGTH: 22
<212> TYPE: DNA
<213> ORGANISM: Artificial Sequence
<220> FEATURE:
<223> OTHER INFORMATION: ZEBRA_R

<400> SEQUENCE: 6
cccatctaaa cgcctgattt tt                                        22

<210> SEQ ID NO 7
<211> LENGTH: 28
<212> TYPE: DNA
<213> ORGANISM: Artificial Sequence
<220> FEATURE:
<223> OTHER INFORMATION: ZEBRA_P1

<400> SEQUENCE: 7
cattttcaga tgatttggca gcagccac                                  28

<210> SEQ ID NO 8

```
<211> LENGTH: 16
<212> TYPE: DNA
<213> ORGANISM: Artificial Sequence
<220> FEATURE:
<223> OTHER INFORMATION: ZEBRA_P2

<400> SEQUENCE: 8
cttcaacagg aggcgc                                                    16
```

USE OF AT LEAST ONE BIOMARKER FOR THE IN VITRO PROGNOSIS OR DIAGNOSIS OF LYMPHOPROLIFERATIVE EPISODES ASSOCIATED WITH THE EPSTEIN-BARR VIRUS (EBV)

FIELD OF THE INVENTION

The present invention relates to the use of at least one biomarker for the in vitro prognosis or diagnosis of lymphoproliferative episodes associated with the Epstein-Barr virus (EBV) in a patient.

BACKGROUND OF THE INVENTION

The Epstein-Barr virus (EBV) is a virus of the Herpesviridae family which infects 90 to 95% of the world population. EBV, a virus with enveloped double-stranded DNA, preferentially infects the B lymphocytes but is also capable of infecting other cell lines, in particular the T lymphocytes, the macrophages and the epithelial cells. EBV enters the B lymphocytes by means of three essential glycoproteins (gp350/220, gp85 and gp42) allowing it to bind to the CD21 receptor and the molecules of the HMC (Histocompatibility Major Complex) of class II present on the surface of the quiescent B lymphocytes. The primary infection with EBV leads to an activation of the immune system of the host which then presents a standard serological profile, in particular by the production of antibodies of IgG and/or IgM isotypes directed against the viral antigens in particular EBNA (Epstein-Barr Nuclear Antigen), EA (Early Antigen) or VCA (Virus Capsid Antigen). This primary infection, which is generally asymptomatic, can lead to an infectious mononucleosis which resolves itself spontaneously in a few weeks in an immunocompetent patient.

Once the primary infection episode is resolved, EBV enters a latency stage. The EBV genome is circularized and is found again in episomal form in the nucleus of the infected cells. A very restricted number of viral genes is then expressed, which allow the virus not only to maintain its genome during division of the host cell but also to escape the vigilance of the immune system. Among these genes, those encoding the nuclear proteins EBNA-1 (Epstein-Barr Nuclear Antigen-1) required for the episomal replication and the maintenance of the viral genome, EBNA-2 (essential for the B lymphocyte immortalization process), EBNA-3 (involved in the establishment of the latent form of EBV), EBNA-5 (involved in the viral transformation), and the viral membrane proteins LMP-1 (Latent Membrane Protein-1) and LMP-2 play a major role. The non-coding viral RNAs EBER-1 (Epstein-Barr virus Encoded RNA-1) and EBER-2 also perform a key function by preventing the apoptosis of the host cells. In reality several latent forms exist, which correspond to the distinct expression profiles of the aforementioned EBV genes. Form 0, where no EBV gene is expressed, corresponds to the latent form of EBV found in the memory B lymphocytes once the primary infection is resolved; this is the least immunogenic form of EBV which thus allows the virus to completely escape the immune system throughout the life of the patient. Some of these memory B lymphocytes can also contain the latent form I (EBNA-1$^+$/EBERs$^+$) of EBV. The cells infected with the form II-A (EBNA-1$^+$/EBNA-2$^-$/LMP-1$^+$) are found in the germinal centres of the amygdalae of healthy carriers. The latent form II-B (EBNA-1$^+$/EBNA-2$^+$/LMP-1$^-$) corresponds to that found in the cells of the amygdalae of carriers suffering from infectious mononucleosis. The latent form III (expression of six EBNA proteins and three LMP proteins) constitutes the most immunogenic latent form of EBV and is generally found in the transformed cells in immunodeficient patients. This latent form of EBV is also considered as the most aggressive because it constitutes the only one to be able to effectively transform B lymphocytes in vitro.

The involvement of the different latent forms of EBV has been reported in numerous neoplastic-type pathologies (Burkitt's lymphoma, Hodgkin's and non-Hodgkin's lymphoma, nasopharyngeal carcinoma and gastric carcinoma, lymphoproliferative syndromes) not only in immunosuppressed or immunodeficient patients, but also in patients having an intact immune system (Carbon et al., The Oncologist 2008, 13: 577-585). However, immunocompetent individuals keep a latent viral infection under control (periodic reactivations of EBV well contained by the immune system), while immunosuppressed or immunodeficient individuals suffer viral reactivations capable of developing into malignant lymphoproliferations.

Lymphoproliferations represent a frequent complication which is most often lethal in patients with immune deficiency, whether of genetic origin (Wiskott-Aldrich's syndrome, X-linked lymphoproliferative syndrome), caused by an infection with the human immunodeficiency virus (HIV) or linked to immunosuppressive treatments in the case of transplant patients. For this last category of patients, the chronic antigenic stimulation linked to a transplant, the oncogenic effect of immunosuppressive treatments, the reduction in immune responses and EBV infection are among the factors that contribute to the development of such lymphoproliferation.

The post-transplant lymphoproliferative diseases (PTLDs) constitute a complication which is often fatal in patients having received a solid organ transplant or a transplant of haematopoietic stem cells. In patients having received a bone marrow transplant, PTLDs occur in the 12 months following the implantation of the transplant, i.e. before the T system is completely restored. Patients who have received transplants can develop PTLDs during the first year following the transplant (when the immunosuppressive treatment is most intense) but also during an episode of chronic prolonged immunosuppression (Ethel Cesarman, Cancer Letters 2011, 305(2): 163-172). PTLDs are characterized by uncontrolled proliferation of the B lymphocytes infected with EBV. In these immunosuppressed patients, hyporeactivity of the T lymphocytes promotes a polyclonal then monoclonal proliferation of B lymphocytes leading to malignancy.

The aforementioned pathologies develop as a result of EBV reactivation. This reactivation corresponds to the activation of the overall replication of EBV involving not only the latent origin of replication (oriP, which allows it to remain in the episomal form) but also the lytic origin of replication (oriLyt) of the virus. While the activation of oriP is carried out by the proteins of cellular origin associated with EBNA-1, that of oriLyt requires the intervention of several proteins of viral origin (Fixman et al., 1995, 69(5): 2998-3006). The activation of oriLyt leads to several consecutive cycles of replication of the viral DNA. EBV reactivation is characterized by strong replication involving both origins of replication of the virus.

During EBV reactivation, a minority of B lymphocytes infected with EBV in its latent form enter a lytic infection phase. During this phase, all of the viral proteins of EBV are produced, allowing the assembly of complete virions which lyse their host cells in order to then infect neighbouring cells (lytic cycle). The purpose of this horizontal transmission of EBV is to increase the pool of B lymphocytes infected with the EBV virus. In a lymphoproliferative context, the cells infected with the lytic form of EBV contribute to the process of tumour progression leading to lymphomas (Hong et al., J. Virology 2005, 79(22): 13993-14003/Ma et al., J. Virology 2011, 85(1): 165-177). These viral reactivations generally have no consequences in immunocompetent patients but can lead to malignant lymphoproliferation in immunodeficient or immunosuppressed patients, which can result in a lymphoma.

The triggering of EBV reactivation is poorly understood. It has however been clearly demonstrated that the viral ZEBRA protein (BamHI Z EBV replication activator), also called Zta, plays a role well upstream of this reactivation (George Miller, 1989 The Yale Journal of Biology and Medicine, 62: 205-213, El-Guindy et al., PLos Pathogens 2010, 6(8): e1001054). The ZEBRA protein, encoded by the BZLF-1 gene, is a transcription factor of the basic leucine-zipper family which plays an essential role in the transcription of the viral genes but also in the activation of virus replication. The ZEBRA protein is responsible for the passage of EBV from its latent phase to its lytic phase. The protein comprises three distinct functional domains: a trans-activation domain, a DNA binding domain and a dimerization domain (Petosa et al., Molecular Cell 2006, 21(4): 565-572). This last domain, called ZANK domain (ZEBRA ANKryn-like Region) not only allows the ZEBRA protein to homodimerize but also to bind the p53 and NF-kB proteins (Dreyfus et al. Virology Journal 2011, 8:422). The interaction of the ZEBRA protein with the p53 and NF-kB proteins could play a role in the immunopathology and the viral carcinogenesis of the B lymphocytes induced by the EBV and other cell lines transitionally infected with the EBV.

The overexpression of the ZEBRA protein in cell lines of lymphocytes leads to the formation of ZEBRA-ZAP or ZEBRA-RACK1 protein dimers capable of modulating the transactivating activity of the ZEBRA protein or of disrupting the transduction of the protein kinase C-dependant signal respectively (Katz et al., PNAS, 1992, 89, 378-382; Tardif et al., JBC, 2002, 277(27), 24148-24154). However, these protein dimers have a purely intracellular location, either in the cytosol or in the nucleus of the cells overexpressing the ZEBRA protein; these dimers are absent from the culture medium. Access to these dimers is only possible following lysis of the cells, making their antibody assay indirect.

The study of pathologies in connection with EBV reactivation has made possible the identification of biological markers allowing the prognosis or diagnosis of lymphoproliferations in patients. Among these markers, ZEBRA constitutes a marker relevant to EBV reactivation.

Biologically, EBV reactivation has been characterized by the titration of anti-ZEBRA antibodies in patients who are carrying Hodgkin's disease (Drouet et al., J. Med. Virol. 1999, 57(4):383-9). The detection of anti-ZEBRA antibodies also constitutes a prognostic marker in patients suffering from nasopharyngeal carcinoma (Tedeschi et al., Clinical and Vaccine Immunology 2007, 14(4): 435-441/Dardari et al., J. Clin. Virol. 2008, 41(2): 96-103). Detection of the ZEBRA antigen has also served as a diagnostic marker of PTLD in patients who have received transplants. However, its measurement requires the performance of biopsies on which immunohistochemical techniques are carried out (Oertel et al., B. J. Haematology 2002, 118:1120-1123). Recourse to such techniques can only be envisaged in cases where the lymphoproliferation is located at a precise site in the organism and not diffused through different tissues.

Molecular biology techniques have made possible the emergence of commercial in vitro diagnostic tests for measuring the viral load of EBV. This measurement does not in itself constitute a marker for the diagnosis of PTLD but constitutes a diagnostic indicator informing the practitioner of the need to use or not use antivirals. However, the techniques used are not very standardized and vary from one analysis centre to another (Preiksaitis et al., Am. J. Transplant. 2009, 9(2): 269-279). In addition, work by Oertel shows that measurement of the viral load is not a good predictive marker of PTLDs (Oertel et al., 2006, Ann. Haematol., 85(7): 478-484).

As a result a real need exists for the identification of diagnostic markers of EBV reactivation which, when associated with other biological markers which are already known, allow the prognosis or diagnosis of lymphoproliferative episodes, whether a first episode or also a relapse.

SUMMARY OF THE INVENTION

One of the purposes of the present invention is to provide a biomarker which is both an early marker of EBV reactivation and which, when associated with other biomarkers, can allow the prognosis or diagnosis of a lymphoproliferation.

Another purpose of the invention is to provide a process for detecting said biomarker which is easy to implement, is non-invasive and the cost of which does not constitute a factor which limits its use.

Yet another purpose of the invention is to provide diagnostic kits which can be used for the prognosis or diagnosis of lymphoproliferative episodes in patients who are seropositive for EBV.

Finally, a purpose of the invention is to provide a biomarker which can be used both in immunosuppressed (or immunodeficient) patients and in immunocompetent patients.

DETAILED DESCRIPTION OF THE INVENTION

The present invention relates to a protein complex isolated from its natural medium and comprising the ZEBRA protein of sequence SEQ ID NO: 1, said isolated protein complex having the following properties:
  it is more stable than the ZEBRA protein, in particular it is more resistant to the action of the proteases than the ZEBRA protein,
  it is capable of specifically binding the AZ125 and AZ130 monoclonal antibodies,
  it is soluble in a body fluid, and in particular a body fluid selected from the group constituted by blood and serum.

The present invention also relates to a protein complex isolated from its natural medium and comprising the ZEBRA protein of sequence SEQ ID NO: 1, said isolated protein complex having the following properties:
  it is more stable than the ZEBRA protein, in particular it is more resistant to the action of the proteases than the ZEBRA protein,
  it is capable of specifically binding the AZ125 and AZ130 monoclonal antibodies,
  it is soluble in a body fluid originating from patients who are seropositive for EBV, and in particular a body fluid selected from the group constituted by blood and serum, it is in a form circulating in said body fluid originating from patients who are seropositive for EBV, it can be assayed directly in said body fluid originating from patients who are seropositive for EBV.

The inventors have, for the first time, demonstrated the existence of a circulating form of the ZEBRA protein in a protected form (protein complex). In addition, the inventors have shown that the ZEBRA antigen in its protected circulating form could be assayed directly from whole blood samples of patients who are seropositive for EBV.

By "protein complex", is meant the physical combination of at least two proteins, one of which must be the ZEBRA protein. The physical combination of the ZEBRA protein with a nucleic acid is also meant. In the present invention, the ZEBRA protein is the native viral protein. By "native viral protein", is meant the protein sequence encoded by a portion of nucleic acids comprised within the EBV genome. The physical combination of the ZEBRA protein with another protein or of the ZEBRA protein with a nucleic acid relies on the non-covalent bonds between the polypeptide chains of said proteins or between the polypeptide chain of the ZEBRA protein and specific sequences of the nucleic acid. This combination would make it possible not only to protect the ZEBRA protein from the action of the proteases but also leave accessibility to the antigenic fragments of the ZEBRA protein recognized by the AZ125 and AZ130 monoclonal antibodies.

By "isolated from its natural medium", is meant a protein complex which has been substantially separated from or purified of the other components of the body fluid, i.e. other blood or serum constituents of a protein, lipidic or glucidic nature. The term "isolated from its natural medium" does not cover a protein complex comprising a recombinant form of the ZEBRA protein. By way of examples and without restricting the subject-matter of the present invention, the purification of the protein complex comprising the ZEBRA protein of the present invention can be carried out using one of the following techniques:

(i) ion exchange chromatography: dialysis of the biological sample, in particular of the plasma against a 0.1M Tris alkaline buffer, pH 8, then passing through a DEAE cellulose column Elution of the protein complex comprising the ZEBRA protein is carried out with a discontinuous gradient of NaCl (0.1M-0.15 M-0.25M-0.5M-0.75M-1M). The fractions collected are analyzed by SDS-PAGE electrophoresis and staining with Coomassie blue; or (ii) SUPERDEX S200 gel-filtration chromatography. This technique which does not require elution can optionally be combined with the method described in (i) in order to increase the degree of ZEBRA purity; or (iii) affinity chromatography: protein A or protein G column on which the purified anti-ZEBRA monoclonal antibodies AZ125 and/or AZ130 are fixed. The dialyzed preparation is deposited on the column, then subjected to elution using 0.1M citric acid, pH 3. The eluate is analyzed by SDS-PAGE and mass spectrometry and MALLS (multiangle laser light scattering) in order to define the molecular mass. A variant of this technique consists of using activated sepharose beads on which the antibodies AZ125 and/or AZ130 are fixed.

By "ZEBRA protein of sequence SEQ ID NO: 1", is meant the protein of 245 amino acids comprising or consisting of SEQ ID NO: 1. The variants of the ZEBRA protein are also meant, i.e. its homologous proteins having SEQ ID NO: 1, said proteins having at least 50% identity with the protein region containing amino acids from 176 to 194 of SEQ ID NO: 1, said region corresponding to the DNA binding domain of the ZEBRA protein.

By "the ZEBRA protein", is meant the ZEBRA protein alone, in its native or recombinant form, i.e. not bound to at least one other protein or one other constituent. By "recombinant protein", is meant a protein produced by a host cell into which an expression vector comprising the sequence encoding the protein of interest has been introduced. The techniques of cloning and production of recombinant proteins are well known to a person skilled in the art. In the case of the present invention, by "recombinant ZEBRA protein", is meant the protein comprising or consisting of SEQ ID NO: 1, and also its homologous proteins having SEQ ID NO: 1, said proteins having at least 50% identity with the protein region containing the amino acids from 176 to 194 of SEQ ID NO: 1, said region corresponding to the DNA binding domain of the ZEBRA protein.

By "more stable", is meant the ability of the complex comprising the ZEBRA protein to retain its functional properties over time. According to the present invention, the half-life of the complex comprising the ZEBRA protein is greater than that of the non-complexed ZEBRA protein. When it is found in the protein complex the ZEBRA protein retains a structured state. Conversely, the tertiary structure of the non-complexed ZEBRA protein is more rapidly destabilized. This stability can be assessed after purification of the protein complex by affinity chromatography on a column containing an anti-ZEBRA antibody. The physico-chemical analysis techniques are well known to a person skilled in the art (Flamand et al., 1999, J. Virol., 73(7): 6104-6110), and are based in particular on experiments involving dissociation of the isolated complex, purified using detergent, analysis by X-ray diffraction or by NMR spectroscopy (Nuclear Magnetic Resonance), or any other technique well-known to a person skilled in the art.

By "more resistant", is meant the ability of the ZEBRA protein in the protein complex to resist the different degradation pathways of the proteins in the eukaryotic cells. These include in particular proteases, lysosome or also the ubiquitine-proteasome pathway.

By "capable of specifically binding the AZ125 and AZ130 monoclonal antibodies", is meant antibodies which substantially bind a single target. In the case of the present invention, the murine AZ125 and AZ130 monoclonal antibodies are specifically directed against the N and C terminal fragments of the ZEBRA protein (FIG. 1). The protein complex comprising the ZEBRA protein is capable of binding to these antibodies and to other monoclonal or polyclonal antibodies directed specifically against immunogenic epitopes of the ZEBRA protein in order to form an immune complex but cannot bind antibodies directed against antigens having no common structure with this complex.

The AZ125 monoclonal antibody is available from the company Argene ITS (Verniolle-France) under the trade name purified anti-EBV-ZEBRA, under the reference 11-007. AZ125 is directed against the peptide 1-140 of the ZEBRA protein, i.e. against exon 1 which encodes the transactivation domain of the ZEBRA protein.

The hybridoma secreting the AZ130 monoclonal antibody was deposited at the CNCM (Collection Nationale de Culture de Microorganismes, Institut Pasteur, 25 rue du Docteur Roux, 75724 Paris Cedex 15, France) under the Budapest Treaty on 17 Nov. 2011, under the reference CNCM 1-4554, said hybridoma and said AZ130 antibody also form part of the present invention.

AZ130 is directed against the peptide 176-194 of the ZEBRA protein, i.e. against exon 2 which encodes the DNA binding domain of the ZEBRA protein.

The present invention also relates to an antibody which specifically binds the C terminal fragment of the ZEBRA protein of sequence SEQ ID NO: 1.

By "C terminal fragment", is meant the peptide of 39 amino acids the sequence of which includes the amino acids 157 to 195 of the ZEBRA protein of SEQ ID NO: 1.

The present invention also relates to a hybridoma deposited at the CNCM (Collection Nationale de Culture de Microorganismes, Institut Pasteur, 25 rue du Docteur Roux, 75724 Paris Cedex 15, France) under the Budapest Treaty on 17 Nov. 2011, under the reference CNCM 1-4554, capable of secreting the AZ130 antibody.

By "soluble in a body fluid", is meant the ability of the complex comprising the ZEBRA protein neither to form aggregate, nor to precipitate in a body fluid at physiological pH. A study of the dispersion of the protein complex in a body fluid can be carried out based on the isolated and purified protein complex, in particular by small-angle X-ray scattering or by any other technique well known to a person skilled in the art.

By "in a circulating form", is meant the protein complex isolated from its natural medium and comprising the ZEBRA protein which is found outside the cells, i.e. it circulates freely in the body fluids. The "circulating form" means that the complex is not located in any of the intracellular compartments but is found in the extracellular medium.

By "directly assayable", is meant the possibility of forming an immune complex between the protein complex isolated from its natural medium and comprising the ZEBRA protein and the AZ125 and/or AZ130 antibodies without it being necessary to carry out cell lysis which would allow the release of said complex into the extracellular medium as is the case for the protein dimers known from the prior art which include the ZEBRA protein.

The invention also relates to a protein complex comprising the ZEBRA protein and having the abovementioned properties, capable of being obtained by purification from the extracellular medium of a culture of cells infected with the Epstein-Barr virus (EBV).

The cells of the Akata line were isolated from a patient suffering from Burkitt's lymphoma. This cell line, which has integrated EBV in its episomal form, is one of the most significant lines in terms of ability to produce EBV. Under standard culture conditions, the cells of the Akata line remain in the latent state. The assay of the ZEBRA antigen is then less than 0.15 µg/ml of culture supernatant. This corresponds to a weak replication phase for EBV during which only oriP is activated. This weak replication phase does not allow the detection of EBV. When they are activated using antibodies of the human anti-IgG type, the cells enter the lytic phase and thus allow the release of viral particles of EBV into the extracellular medium. The assay of the ZEBRA antigen is then approximately 2.67 µg/ml of culture supernatant. This corresponds to a strong replication phase for EBV during which the two origins of viral replication oriP and oriLyt are activated.

Thus, according to a particular embodiment, said culture is the culture of a cell line belonging to the group constituted by all appropriate cell lines for infection with the replicative form of EBV, and in particular the Akata line.

By "replicative form", is meant the form of EBV where the two origins of replication oriP and oriLyt are activated. It is the viral form leading to the production of complete viral particles capable of infecting cells in culture. This replicative form is characteristic of EBV reactivation.

The inventors have demonstrated that the levels of circulating ZEBRA protein vary depending on the state of reactivation of the EBV virus, and that this protein is found at a high level in the whole blood of patients capable of developing a lymphoproliferation.

The present invention also relates to a process for detecting, in a biological sample originating from a patient seropositive for EBV, a protein complex comprising the ZEBRA protein and having the abovementioned properties, said process comprising the stages:

(a) of obtaining a biological sample originating from a patient seropositive for EBV, (b) of determining the presence of an immune complex, said immune complex being constituted by the aforementioned protein complex bound to one of the following ligands: AZ125 antibody, AZ130 antibody or AZ125 and AZ130 antibodies used in combination, by comparison with a biological sample originating from a patient seronegative for EBV.

According to another embodiment the process for detecting, in a biological sample in particular selected from the group constituted by blood and serum originating from a patient seropositive for EBV, a protein complex comprising the ZEBRA protein and having the abovementioned properties, comprises the following stage:

determining the presence of an immune complex in a biological sample collected beforehand from a patient seropositive for EBV, said immune complex being constituted by the aforementioned protein complex bound to one of the following ligands: AZ125 antibody, AZ130 antibody or AZ125 and AZ130 antibodies used in combination, by comparison with a biological sample collected beforehand from a patient seronegative for EBV.

By "patient seropositive for EBV", is meant a patient who has been infected with the EBV virus and whose serological profile shows that this is not a primary infection but an old infection. In other words, the patient is not suffering from infectious mononucleosis but is a carrier of the EBV virus mainly in its latent form. The serological profile is based on the detection of anti-EBV protein antibodies well-known to a person skilled in the art. These are in particular anti-VCA IgG and IgM, anti-EA IgG or anti-EBNA IgG. The serological profile can be standard or atypical depending on the state of the patient's immune system. By "patient", is meant a mammal, in particular a human being or an animal.

By "obtaining a biological sample", is meant the stage of collection of said biological sample carried out directly on the patient seropositive for EBV.

By "immune complex", is meant the physical interaction between an antigen and an antibody specifically directed against this antigen. In the present invention, this interaction is carried out in vitro between the protein complex comprising the ZEBRA protein and the murine AZ125 and/or AZ130 monoclonal antibodies, specifically directed against the N and C terminal fragments of the ZEBRA protein.

According to a particular embodiment, the process of the invention can be implemented on a biological sample selected from the group constituted by blood and serum.

According to a more particular embodiment, in the aforementioned process of the invention, the binding of the protein complex to one of the ligands is detected using an immunoassay-type test.

According to an even more particular embodiment, in the aforementioned process of the invention, the immunoassay is of the sandwich ELISA type in which the AZ125 antibody is adsorbed on a suitable plate and the AZ130 antibody is used for detecting the binding of the protein complex to the adsorbed AZ125 antibody.

The formation of the immune complex can take place between the protein complex comprising the ZEBRA protein and only one of the two murine AZ125 or AZ130 monoclonal antibodies.

The formation of the immune complex can take place between the protein complex comprising the ZEBRA protein and the two murine AZ125 and AZ130 monoclonal antibodies.

The implementation of the immunodetection test is well-known to a person skilled in the art. The antigen detection and assay can be carried out by sandwich or competitive immunocapture. The means of detection are generally anti-human heterologous antibodies coupled either to an enzyme capable of catalyzing a colour reaction or to a fluorescent or luminescent marker.

The detection of the level of the ZEBRA protein in patients can be associated with at least one of the other biological markers that are relevant in terms of infection of the patient with the EBV virus.

According to another embodiment, the process of the invention also comprises the detection of anti-ZEBRA antibodies.

By "anti-ZEBRA antibodies", is meant all the antibodies synthesized by the immune system of a patient seropositive for EBV, specifically directed against the ZEBRA viral protein. The detection of these antibodies can be carried out using a recombinant form of the ZEBRA protein or of the natural or synthetic peptides derived directly from the sequence of the ZEBRA protein.

The detection of the anti-ZEBRA antibodies can be carried out on the same sample as that used for the detection of the protein complex comprising the ZEBRA protein, or on another sample (of the same kind or of a different kind, in particular a biopsy) collected on the same day as that of the detection of the protein complex comprising the ZEBRA protein.

The detection of the protein complex comprising the ZEBRA protein can be associated with the detection of the anti-ZEBRA antibodies.

According to another embodiment, the process of the invention also comprises measurement of the viral load of EBV in a biological sample from the patient.

By "viral load", is meant the detection of the EBV genome in a patient seropositive for this virus. The quantification of the nucleic acid of EBV can be absolute or relative. The quantification unit can be expressed in copies/ml, copies/µg of cellular DNA which is equivalent to copies/150,000 cells (1 µg represents 150,000 cells) or in IU (International Unit)/ml (First WHO International Standard for EBV, NIBSC 09/260).

The measurement of the viral load can be carried out on the same sample as that used for the detection of the protein complex comprising the ZEBRA protein, or on another sample (of the same kind or of a different kind, in particular a biopsy) collected on the same day as that of the detection of the protein complex comprising the ZEBRA protein.

The detection of the protein complex comprising the ZEBRA protein can be associated with measurement of the viral load.

The detection of the protein complex comprising the ZEBRA protein can be associated with measurement of the viral load and detection of the anti-ZEBRA antibodies.

According to a particular embodiment, in the process of the invention the viral load is detected by a PCR-type technique.

By "PCR", is meant the polymerase chain reaction which allows the amplification of a nucleic acid in vitro into a large number of copies identical to each other and identical to the nucleic acid used as amplification matrix.

In the prior art a pair of primers and a probe exist, allowing the detection of the BALF-5 gene encoding the EBV DNA polymerase (Kimura et al., J Clin Microbiol. 1999 January; 37(1):132-6). The sequences of these primers and this probe correspond to the sequences SEQ ID NO: 2 for the sense primer, SEQ ID NO: 3 for the anti-sense primer and SEQ ID NO: 4 for the probe respectively. The nucleotide sequences are shown in Table 2 of Example 2 of the present application.

Moreover, the inventors have also selected a pair of primers and two probes allowing the detection of the BZLF-1 gene encoding the ZEBRA viral protein of EBV. The sequence of the B95-8 strain of the EBV genome used for the selection of the primers and probes can be accessed in the databases under the reference GenBank V01555.2. The sequences of these primers and this probe correspond to the sequences SEQ ID NO: 5 for the sense primer, SEQ ID NO: 6 for the anti-sense primer and SEQ ID NO: 7 or SEQ ID NO: 8 for the probe respectively. The nucleotide sequences are shown in Table 2 of Example 2 of the present application.

According to a particular embodiment, in the process of the invention a PCR is implemented using primers and probes the nucleic acid sequences of which are selected from the group constituted by: SEQ ID NO: 2, SEQ ID NO:3, SEQ ID NO:4.

According to another particular embodiment, in the process of the invention a PCR is implemented using primers and probes the nucleic acid sequences of which are selected from the group constituted by: SEQ ID NO: 5, SEQ ID NO: 6, SEQ ID NO: 7, SEQ ID NO: 8.

According to yet another particular embodiment, in the process of the invention a PCR is implemented using primers and probes the nucleic acid sequences of which are selected from the group constituted by: SEQ ID NO: 2, SEQ ID NO: 3, SEQ ID NO: 4, SEQ ID NO: 5, SEQ ID NO: 6, SEQ ID NO: 7, SEQ ID NO: 8.

By "primers and probes", is meant nucleic acid sequences varying from 8 to 30 oligonucleotides. The primers are capable of hybridizing to a DNA sequence which is complementary to them, to form a DNA-DNA hybrid. The DNA polymerase can then extend the DNA strand downstream of the primer. A probe is a nucleic acid sequence bound to a detection means, in particular a fluorophore. The primer and probe design techniques are molecular biology techniques well known to a person skilled in the art (Molecular Cloning: A laboratory Manual, CHSL, New York, 1989/Current Protocols in Molecular Biology, John Wiley & Its, New York, 1998).

The inventors have shown that, in lymphoblastoid lines infected with EBV, at the time of reactivation of the virus, the ZEBRA protein is capable of activating the promoter of the gene encoding IL-10 resulting in an increase in the expression of this cytokine and its release into the extracellular medium. The IL-10 has an immunomodulatory activity and promotes the proliferation of the B lymphocytes. Consequently, it appears relevant to monitor changes in the concentration of this cytokine in patients.

According to another embodiment, the process of the invention also comprises assay of the interleukin-10 (IL-10) in a biological sample from the patient.

By "interleukin 10", is meant the cytokine capable of inhibiting the production of interferon-γ and the synthesis of pro-inflammatory cytokine such as IL-1, IL-6 and TNF-α (Tumor Necrosis Factor-alpha). The IL-10 assay can be carried out using antibodies specifically directed against this cytokine.

The IL-10 assay can be carried out on the same sample as that used for the detection of the protein complex comprising the ZEBRA protein, or on another sample (of the same kind or of a different kind, in particular a biopsy) collected on the same day as that of the detection of the protein complex comprising the ZEBRA protein.

The detection of the protein complex comprising the ZEBRA protein can be associated with the IL-10 assay.

The detection of the protein complex comprising the ZEBRA protein can be associated with the IL-10 assay and detection of the anti-ZEBRA antibodies.

The detection of the protein complex comprising the ZEBRA protein can be associated with the IL-10 assay and measurement of the viral load.

The detection of the protein complex comprising the ZEBRA protein can be associated with the IL-10 assay, detection of the anti-ZEBRA antibodies and measurement of the viral load.

The present invention also relates to the use of the detection of the presence of a protein complex isolated from its natural medium and comprising the ZEBRA protein of sequence SEQ ID NO: 1, said isolated protein complex having the following properties:
  it is more stable than the ZEBRA protein, in particular it is more resistant to the action of the proteases than the ZEBRA protein,
  it is capable of specifically binding the AZ125 and AZ130 monoclonal antibodies,
  it is soluble in a body fluid, and in particular a body fluid selected from the group constituted by blood and serum,
in a biological sample from a patient seropositive for EBV, for the prognosis or diagnosis of a lymphoproliferation associated with the replicative form of EBV or more generally of a tumour associated with EBV, in particular nasopharyngeal cancer.

The present invention also relates to a method for the in vitro and/or ex-vivo prognosis or of diagnosis of a lymphoproliferation associated with the replicative form of EBV or more generally of a tumour associated with EBV, in particular nasopharyngeal cancer, said method requiring detection of the presence of a protein complex comprising the ZEBRA protein and having the abovementioned properties, in a biological sample from a patient seropositive for EBV.

This lymphoproliferation is a direct consequence of EBV reactivation characterized by the activation of the two origins of viral replication oriP and oriLyt. This process leads to a strong replication of EBV.

By "lymphoproliferation", is meant an uncontrolled multiplication of abnormal lymphocytes, originating from the B line or from the T line. By "uncontrolled", is meant the inability of the immune system to destroy the surplus abnormal lymphocytes. In the case of the B lineage, this multiplication can be the consequence of the immortalization of the B lymphocytes by the EBV virus.

According to a particular embodiment, in the use of the invention, the quantity of protein complex for the prognosis or diagnosis of a lymphoproliferation is approximately equal to or greater than 0.15 micrograms/ml of biological sample.

According to another particular embodiment, in the method for the in vitro and/or ex-vivo prognosis or diagnosis of a lymphoproliferation associated with the replicative form of EBV or more generally of a tumour associated with EBV, in particular nasopharyngeal cancer, the quantity of protein complex for the prognosis or diagnosis of a lymphoproliferation is approximately equal to or greater than 0.15 micrograms/ml of biological sample.

According to a more particular embodiment, in the use of the invention, the prognosis occurs within a time interval varying from 1 to 90 days before the clinical confirmation of a lymphoproliferation.

According to a particular embodiment, in the use of the invention, the immunological status of the patient belongs to the group: immunocompetent patient, immunosuppressed patient or immunodeficient patient.

By "immunocompetent patient", is meant a patient whose immune system completely fulfils its functions of defence of the organism against the "non-self", i.e. infections caused by microorganisms, in particular bacteria, viruses, yeasts and fungi. An immunocompetent patient within the meaning of the present invention, who is seropositive for EBV, has a conventional serological profile vis-à-vis the viral markers EBNA, VCA and EA: IgG anti-VCA positive/IgM anti-VCA negative/IgA anti-VCA negative/IgG anti-EA negative/IgG anti-EBNA positive.

By "immunosuppressed patient", is meant a patient whose immune system is functioning imperfectly. This is in particular the case with a patient awaiting or having received a transplant who has received immunosuppressive treatment. In this case, it is a chemical treatment that causes the dysfunction of the immune system.

By "immunodeficient patient", is meant a patient whose immune system is functioning imperfectly. This is in particular the case with a patient presenting a pathology of Wiskott-Aldrich syndrome type or an X-linked lymphoproliferative syndrome type or suffering from any other pathology involving the immune system. This is also the case with a patient infected with a virus disrupting the immune system, in particular with the human immunodeficiency retrovirus (HIV), the human T lymphotropic virus (HTLV) or the Xenotropic MuLV-related virus (XMRV). In this case, the dysfunction of the immune system is closely linked to the physiological or physiopathological state of the patient.

An immunosuppressed or immunodeficient patient does not have all of the players in the immune response. A deficit in one or more of the cell lineages of the immune system disrupts the defence system of the patient in the fight against pathogenic agents. Immunosuppression can alter the B lineage and/or the T lineage.

An immunosuppressed or immunodeficient patient within the meaning of the present invention, who is seropositive for EBV, can have an atypical serological profile vis-à-vis the viral markers EBNA, VCA and EA. By way of example and without restricting the idea of the present invention, the following serological profile is considered atypical by clinicians: IgG anti-VCA positive/IgM anti-VCA negative/IgA anti-VCA positive/IgG anti-EA negative/IgG anti-EBNA positive. An immunosuppressed or immunodeficient patient who is seropositive for EBV generally has lower anti-EBV antibody titres than those observed in an immunocompetent patient who is seropositive for EBV.

According to a more particular embodiment, in the use of the invention, the patient is immunosuppressed or immunodeficient and belongs in particular to the group constituted by: a patient awaiting a transplant, a patient having received a transplant, a patient seropositive for an immunosuppressive virus such as HIV, or a patient presenting a genetically transmitted immunological deficit.

According to another particular embodiment, in the method for the in vitro and/or ex-vivo prognosis or diagnosis of a lymphoproliferation associated with the replicative form of EBV or more generally of a tumour associated with EBV, in particular nasopharyngeal cancer, the patient is immunosuppressed or immunodeficient and belongs in particular to the group constituted by: a patient awaiting a transplant, a patient having received a transplant, a patient seropositive for an immunosuppressive virus such as HIV, or a patient presenting a genetically transmitted immunological deficit.

According to a particular embodiment, the use of the invention allows the prognosis or diagnosis of a first episode of lymphoproliferation, in which the quantity of protein complex varies from 1 to 100 micrograms/ml of biological sample, said first episode of lymphoproliferation occurring before the initiation of any therapeutic treatment of a lymphoma.

By "first episode of lymphoproliferation", is meant the identification of a lymphoproliferation by a clinician, on the basis of biological markers and the general state of the patient. This first episode corresponds to the first diagnosis of lymphoproliferation following the transplant.

By "before the initiation of any therapeutic treatment of a lymphoma", is meant the time interval which has elapsed between the transplant and the first diagnosis of lymphoma. During this period, the patient receives neither anti-viral treatment nor treatment targeting the destruction of part of the pool of B lymphocytes infected with EBV.

According to a particular embodiment, the use of the invention also comprises detection of the anti-ZEBRA antibodies.

By "anti-ZEBRA antibodies", is meant the antibodies produced by the immune system of the patient infected with EBV specifically directed against the ZEBRA antigen. These antibodies are incapable of binding to other antigens with the same affinity as that which characterizes the ZEBRA antigen anti-ZEBRA antibody bond.

The result of the detection of the anti-ZEBRA antibodies can be expressed in a relative manner (positive/negative) or in the form of a titre, i.e. corresponding to the serial dilution limit, starting from which a positive sample becomes negative. According to a more particular embodiment, in the use of the invention, the EBV viral load is also determined in a biological sample originating from the aforementioned patient.

By "viral load", is meant the number of copies of viral genome found in a sample originating from a patient seropositive for EBV. This measurement can be carried out by searching for one of the viral genes present in the EBV genome using specific primers and probes. The unit of measurement of the viral load can be expressed in copies/ml of sample, copies/µg of cellular DNA which is equivalent to copies/150,000 cells (1 µg represents 150,000 cells) or in IU (International Unit)/ml (First WHO International Standard for EBV, NIBSC 09/260).

According to an even more particular embodiment, in the use of the invention the viral load linked to a lymphoproliferation is approximately equal to or greater than $10^4$ copies per 150,000 cells, and preferably comprised within a range varying from $10^4$ to approximately $10^9$ copies per 150,000 cells.

According to another more particular embodiment, in the use of the invention the viral load linked to a lymphoproliferation is approximately equal to or greater than $3.2 \cdot 10^4$ copies/ml of body fluid, said body fluid being in particular blood or serum.

According to a particular embodiment, the use of the invention also comprises an IL-10 assay in the biological sample.

By "IL-10", is meant interleukin-10 of human (hIL-10) or animal origin (aIL-10). The synthesis of this cytokine can be activated by viral proteins of EBV. The measurement of the IL-10 level can be expressed in a relative (negative/positive) or quantificative manner (pg/ml of sample or any other unit).

According to a more particular embodiment, in the use of the invention the quantity of IL-10 linked to a lymphoproliferation is greater than approximately 100 picograms/ml, and preferably comprised within a range varying from 100 to 250 picograms/ml.

According to an even more particular embodiment, the use of the present invention, in which the patient is immunosuppressed or immunodeficient, for the prognosis or diagnosis of a first episode of lymphoproliferation, in which the quantity of protein complex varies from 1 to 100 micrograms/ml of biological sample, said first episode of lymphoproliferation occurring before the initiation of any therapeutic treatment of a lymphoma, which also comprises:

the detection of the anti-ZEBRA antibodies, and
optionally the measurement of the EBV viral load, said viral load linked to a first episode of lymphoproliferation being approximately equal to or greater than $10^4$ copies per 150,000 cells, and preferably comprised within a range varying from $10^4$ to approximately $10^9$ copies per 150,000 cells, and
optionally IL-10 assay, the quantity of IL-10 linked to a first episode of lymphoproliferation being greater than approximately 100 picograms/ml, and preferably comprised within a range varying from 100 to 250 picograms/ml.

According to another more particular embodiment, the method for the in-vitro and/or ex-vivo prognosis or diagnosis according to the present invention, in which the patient is immunosuppressed or immunodeficient, for the prognosis or diagnosis of a first episode of lymphoproliferation, in which the quantity of protein complex varies from 1 to 100 micrograms/ml of biological sample, said first episode of lymphoproliferation occurring before the initiation of any therapeutic treatment of a lymphoma, also comprises:

the detection of the anti-ZEBRA antibodies, and
optionally the measurement of the EBV viral load, said viral load linked to a first episode of lymphoproliferation being approximately equal to or greater than $10^4$ copies per 150,000 cells, and preferably comprised within a range varying from $10^4$ to approximately $10^9$ copies per 150,000 cells, and
optionally IL-10 assay, the quantity of IL-10 linked to a first episode of lymphoproliferation being greater than approximately 100 picograms/ml, and preferably comprised within a range varying from 100 to 250 picograms/ml.

According to a particular embodiment, the use of the invention allows the prognosis or diagnosis of a reactivation of the replicative form of EBV occurring following a treatment of the patient for a first episode of lymphoma associated with EBV reactivation.

By "reactivation", is meant passage from the latent form of EBV to the lytic form. The ZEBRA protein serves as "interrupter" in the sense that it will allow the transcription of the early EBV genes. The products originating from these early genes will in turn be able to induce the expression of the late EBV genes.

In the present case, EBV reactivation occurs when the patient has received a treatment aimed at the mature B lymphocytes infected with one of the latent forms of EBV. This treatment is based in particular on the use of monoclonal antibodies (MabThera/Rituximab) directed against the CD20 antigen present on the surface of the mature B lymphocytes, whether or not they are infected with EBV. EBV reactivation following treatment of the patient is likely to lead to a new episode of lymphoproliferation.

According to a more particular embodiment, in the use of the invention, the quantity of protein complex for the prognosis or diagnosis of a reactivation of the replicative form of EBV is approximately equal to or greater than 0.15 micrograms/ml of biological sample, and preferably comprised within a range varying from 0.15 to 20 micrograms/ml.

According to a particular embodiment, the use of the invention also comprises detection of the anti-ZEBRA antibodies.

According to a more particular embodiment, in the use of the invention, the EBV viral load is also determined in a biological sample originating from the patient.

According to an even more particular embodiment, in the use of the invention, the EBV viral load is approximately equal to or greater than $10^3$ copies per 150,000 cells, and preferably comprised within a range varying from $10^3$ to approximately $10^9$ copies per 150,000 cells.

According to a particular embodiment, the use of the present invention in which the patient is immunosuppressed or immunodeficient, for the prognosis or diagnosis of a reactivation of the replicative form of EBV occurring following treatment of the patient for a first episode of lymphoma associated with EBV reactivation, in which the quantity of protein complex for the prognosis or diagnosis of a reactivation of the replicative form of EBV is approximately equal to or greater than 0.15 micrograms/ml of biological sample, and preferably comprised within a range varying from 0.15 to 20 micrograms/ml, which also comprises:
  detection of the anti-ZEBRA antibodies, and
  optionally measurement of the EBV viral load, said EBV viral load linked to the reactivation of the replicative form of EBV being approximately equal to or greater than $10^3$ copies per 150,000 cells, and preferably comprised within a range varying from $10^3$ to approximately $10^9$ copies per 150,000 cells.

According to another more particular embodiment, the method for the in-vitro and/or ex-vivo prognosis or diagnosis according to the present invention, in which the patient is immunosuppressed or immunodeficient, for the prognosis or diagnosis of a reactivation of the replicative form of EBV occurring following a treatment of the patient for a first episode of lymphoma associated with EBV reactivation, in which the quantity of protein complex for the prognosis or diagnosis of a reactivation of the replicative form of EBV is approximately equal to or greater than 0.15 micrograms/ml of biological sample, and preferably comprised within a range varying from 0.15 to 20 micrograms/ml, also comprises:
  detection of the anti-ZEBRA antibodies, and
  optionally measurement of the EBV viral load, said EBV viral load linked to the reactivation of the replicative form of EBV being approximately equal to or greater than $10^3$ copies per 150,000 cells, and preferably comprised within a range varying from $10^3$ to approximately $10^9$ copies per 150,000 cells.

The use of the present invention can also be envisaged in a immunocompetent patient who is seropositive for EBV.

According to a particular embodiment, in the use of the invention, the patient is immunocompetent and does not present clinical signs of infectious mononucleosis.

According to a more particular embodiment, in the use of the invention, in an immunocompetent patient, the quantity of protein complex for the prognosis or diagnosis of a reactivation of the replicative form of EBV is approximately equal to or greater than 7 micrograms/ml of biological sample.

According to a particular embodiment, the use of the invention in an immunocompetent patient also comprises detection of the anti-ZEBRA antibodies.

According to a more particular embodiment, in the use of the invention, in an immunocompetent patient, the EBV viral load is also determined in a biological sample originating from the patient.

According to an even more particular embodiment, in the use of the invention, in an immunocompetent patient, the viral load linked to a viral reactivation varies from $10^2$ to $10^3$ copies per 150,000 cells.

According to a particular embodiment, the use of the invention in an immunocompetent patient also comprises an IL-10 assay in the biological sample.

According to a more particular embodiment, in the use of the invention, in an immunocompetent patient, the quantity of IL-10 linked to a viral reactivation greater than approximately 100 pg/ml, and preferably comprised within a range from approximately 100 to approximately 250 pg/ml.

According to an even more particular embodiment, the use of the invention in which the patient is immunocompetent and does not present clinical signs of infectious mononucleosis, in which the quantity of protein complex for the prognosis or diagnosis of a reactivation of the replicative form of EBV is approximately equal to or greater than 7 micrograms/ml of biological sample, which also comprises:
  detection of the anti-ZEBRA antibodies, and
  optionally measurement of the EBV viral load, said viral load linked to a reactivation of the replicative form of EBV varying from $10^2$ to $10^3$ copies per 150,000 cells, and
  optionally IL-10 assay, the quantity of IL-10 linked to a reactivation of the replicative form of EBV being greater than approximately 100 pg/ml, and preferably comprised within a range from approximately 100 to approximately 250 pg/ml.

According to another more particular embodiment, the method for the in-vitro and/or ex-vivo prognosis or diagnosis according to the present invention, in which the patient is immunocompetent and does not present clinical signs of infectious mononucleosis, in which the quantity of protein complex for the prognosis or diagnosis of a reactivation of the replicative form of EBV is approximately equal to or greater than 7 micrograms/ml of biological sample, also comprises:
  detection of the anti-ZEBRA antibodies, and
  optionally measurement of the EBV viral load, said viral load linked to a reactivation of the replicative form of EBV varying from $10^2$ to $10^3$ copies per 150,000 cells, and
  optionally IL-10 assay, the quantity of IL-10 linked to a reactivation of the replicative form of EBV being greater than approximately 100 pg/ml, and preferably comprised within a range from approximately 100 to approximately 250 pg/ml.

According to yet another embodiment, in the use of the invention the detection of the presence of the protein complex is repeated over time, the time interval between each detection being 10 days at most, preferably 5 days at most, and more preferably 3 days.

According to another more particular embodiment, in the method for the in-vitro and/or ex-vivo prognosis or diagnosis according to the present invention, the detection of the presence of the protein complex is repeated over time, the time interval comprised between each detection being 10 days at most, preferably 5 days at most, and more preferably 3 days.

The present invention also relates to a protein complex detection kit comprising the ZEBRA protein and having the abovementioned characteristics for the implementation of a process as described previously, said detection kit comprising antibodies specifically directed against the ZEBRA protein, and in particular the AZ125 and/or AZ130 antibodies.

According to another embodiment, said detection kit comprises, in addition to the antibodies specifically directed against the ZEBRA protein:
- antigens allowing the detection of the anti-ZEBRA antibodies, in particular the ZEBRA protein in its recombinant form or peptides derived from SEQ ID NO: 1, and/or
- viral load detection means, these means being preferably constituted by primers the nucleic acid sequence of which is selected from the group constituted by: SEQ ID NO: 2 to SEQ ID NO: 8, and/or,
- means for detecting IL-10, in particular anti-IL10 antibodies.

The present invention also relates to nucleotide sequences of the primers and probes type, for the detection of the Epstein-Barr virus (EBV) by amplification, and the processes using them.

The invention relates to an oligonucleotide consisting of a nucleic acid sequence selected from the group comprising the sequences SEQ ID NO: 5, SEQ ID NO: 6, and their complementary sequences.

By "oligonucleotide", is meant a nucleic acid sequence which can be used as primer in an amplification process or as probe in a detection process. In the present invention, the oligonucleotides consist of a sequence of at least 15, preferably 28 nucleotides, and preferably less than 30 nucleotides, capable of hybridizing to a genomic DNA molecule or to complementary DNA. By "hybridization", is meant the physical interaction existing between two nucleic acid molecules. This hybridization can involve a DNA/DNA or RNA/RNA homoduplex or DNA/RNA heteroduplex.

By "nucleic acid", is meant a succession of nucleotides linked to each other by phosphodiester bonds. A molecule of nucleic acid can be linear, circular, single-stranded, double-stranded, partially double-stranded. The nucleic acid sequences are described in the present invention according to the usage well known to a person skilled in the art, i.e. they are defined by a sequence numbered in the direction 5' towards 3'.

By "complementary sequences", is meant two nucleic acid sequences which have complementary nucleotides that can interact with each other via hydrogen bonds. Opposite an adenine, there is always a thymine; opposite a cytosine, there is always a guanine. By way of example, and without this restricting the scope of the invention, the sequence 5' ATCG 3' and the sequence 5' CGAT 3' are complementary.

The invention also relates to the use of oligonucleotides consisting of a nucleic acid sequence selected from the group comprising the sequences SEQ ID NO: 5, SEQ ID NO: 6 and their complementary sequences, as primers for carrying out hybridization and optionally amplification of a nucleic acid originating from the EBV genome.

By "amplification", is meant increasing the concentration of a specific DNA sequence among a mixture of DNA sequences. The DNA amplification techniques are techniques well known to a person skilled in the art.

The invention also relates to the use of the oligonucleotide consisting of the sequence SEQ ID NO: 7 or its complementary sequence as a probe for carrying out a hybridization with a nucleic acid originating from the EBV genome.

By "EBV", is meant the virus of the genus *Lymphocryptovirus* of the family of the Herpesviridae. The Epstein-Barr virus (EBV), also called HHV-4 (Human Herpes Virus of type 4) has a genome presented in the form of a double-stranded linear DNA of 172,000 base pairs. Several sub-types of EBV exist, called sub-types 1 and 2 or A and B.

According to another embodiment, the oligonucleotide consisting of the sequence SEQ ID NO: 8 or its complementary sequence can be used as a probe in order to carry out a hybridization with a nucleic acid originating from the EBV genome.

The invention also relates to the use of the oligonucleotide consisting of the sequence SEQ ID NO: 7 or its complementary sequence labelled at one end with a fluorophore and optionally at the other end with a quencher.

By "fluorophore", is meant molecules capable of emitting light when they are excited by a light source. The fluorophores are molecules well known to a person skilled in the art, the most used of which are Fam, Tet, Hex, Tamra, Texas Red, Cy3, Cy5. The purpose of this non-exhaustive list is to illustrate the concept of a fluorophore but it must not in any event restrict the present invention to the use of these fluorophores alone.

By "quencher", is meant a chemical species, capable of deactivating an excited state created in a molecular entity by energy or electron transfer, or by a chemical mechanism. The quenchers are molecules well known to a person skilled in the art, the most used of which are Dabcyl, Eclipse Dark Quencher, Black Hole Quencher. A fluorophore can also act as a quencher. For this, the emission spectrum of the fluorophore grafted at the 5' end must not overlap the excitation spectrum of the fluorophore-quencher grafted at the 3' end. The purpose of this non-exhaustive list is to illustrate the concept of quencher but it must not in any event restrict the present invention to the use of these quenchers alone.

In the present invention, the probes used are covered by the Taqman technology definition. The probes are labelled at their 5' end with a fluorophore, for example FAM, and at their 3' end with a quencher, for example TAMRA, which inhibits the emission of the fluorophore when they are in proximity During the PCR, if the probe is hybridized to its target, it is hydrolyzed by the DNA polymerase. The fluorophore thus separated from the quencher emits a signal proportional to the number of hydrolysed probes, measurable at the time of elongation. There are other PCR technologies well known to a person skilled in the art, using in particular FRET (Fluorescent Resonance Energy Transfer), and probes of the Molecular Beacon type or of the Scorpion type.

According to another embodiment, the oligonucleotide consisting of the sequence SEQ ID NO: 8 or its complementary sequence labelled at one end with a fluorophore and optionally to the other end with a quencher can also be used.

Another purpose of the invention is to propose a set of oligonucleotides consisting of the oligonucleotides of sequences SEQ ID NO: 5, SEQ ID NO: 6 and SEQ ID NO: 7.

According to another embodiment, the aforementioned set of oligonucleotides can consist of the oligonucleotides of sequences SEQ ID NO: 5, SEQ ID NO: 6 and SEQ ID NO: 8.

The invention also relates to a process for detecting EBV by in-vitro amplification from a biological sample, said process comprising the stages of:
- bringing the set of oligonucleotides as defined above into contact with a biological sample, or a nucleic acid originating from the aforementioned biological sample, under conditions allowing the oligonucleotides to hybridize to a nucleic acid of EBV present in the aforementioned sample,
- amplification of the nucleic acid of EBV using the oligonucleotides as primers,
- detection of the amplification product characterizing the presence of EBV in the sample.

According to another embodiment, in the EBV detection process, the nucleic acid of EBV is amplified by PCR. The PCR can be qualitative, quantitative or semi-quantitative. Depending on whether or not a detection probe is used, this is referred to as real time PCR or standard PCR.

According to another more particular embodiment, in the EBV detection process, the detection of the amplification product is carried out using the oligonucleotide of sequence SEQ ID NO: 7 or its complementary sequence labelled at one end with a fluorophore and at the other end with a quencher as probe.

According to another more particular embodiment, in the EBV detection process, the detection of the amplification product is carried out using the oligonucleotide of sequence SEQ ID NO: 8 or its complementary sequence, labelled at one end with a fluorophore and at the other end with a quencher, as probe.

The invention also relates to a kit for the amplification of EBV from a biological sample, said kit comprising one of the aforementioned sets of oligonucleotides or their complementary sequences and means allowing the amplification of a nucleic acid of EBV.

According to a particular embodiment, said amplification kit comprises:
- at least one set of oligonucleotides consisting of the oligonucleotides of sequences SEQ ID NO: 5, SEQ ID NO: 6 and SEQ ID NO: 7,
- a means for amplifying a nucleic acid of EBV,
- optionally an internal control.

According to a particular embodiment, said amplification kit comprises:
- at least one set of oligonucleotides consisting of the oligonucleotides of sequences SEQ ID NO: 5, SEQ ID NO: 6 and SEQ ID NO: 8,
- a means for amplifying a nucleic acid of EBV,
- optionally an internal control.

By "means for amplifying a nucleic acid", is meant the dNTPs, Taq Polymerase, salts and buffers which make it possible to carry out a PCR.

By "internal control", is meant a nucleic acid sequence (exogenous DNA) unrelated to the EBV genome, primers and a probe allowing the amplification and the detection of this exogenous DNA. This internal control is placed in the mix used for the PCR for the detection of EBV and evidences the satisfactory operation of the amplification.

LEGEND OF THE FIGURES

FIG. 1: Diagrammatic representation of the different domains of the ZEBRA protein. The protein sequence of the ZEBRA protein numbers 245 amino acids. The different fields of the protein are represented by the blocks:
- A: activation domain, which extends from amino acids 1 to 140,
- B: DNA binding domain, which extends from amino acids 176 to 194,
- C: dimerization field, which extends from amino acids 195 to 221.

The arrows indicate the antigenic epitopes of the ZEBRA protein specifically recognized by the AZ125 and AZ130 antibodies.

The present invention is illustrated by the following examples.

EXAMPLE 1: ASSAY OF THE CIRCULATING ZEBRA ANTIGEN AND ANTI-ZEBRA ANTIBODIES IN NON-IMMUNOSUPPRESSED PATIENTS

1—Patients

A cohort of 14 non-immunosuppressed patients (MST Consultations), seropositive for EBV but having no PTLD were tested and the presence of the ZEBRA antigen or anti-ZEBRA antibodies was assessed.

2—Method of Assay of the ZEBRA Antigen

The technique for detecting the soluble ZEBRA antigen is based on the five-stage ELISA method: (i) coating of a 96-well plate with the AZ 125 antibody (purified, diluted in PBS to a final concentration of 10 µg/ml final). The plate is then placed overnight at 4-8° C. (ii) The plate is washed three times using a solution of PBS containing 0.5% Tween 20, followed by the saturation of the non-specific sites of the wells by adding saturation buffer (PBS-Tween 20 0.05%-FCS 10%-BSA 2%) for 60 minutes at ambient temperature under stirring. The plate is again rinsed three times. (iii) 100 µl of serum previously diluted to 1/10 in dilution buffer (PBS-Tween 20 0.05%-FCS 10%) are added twice. In parallel, a standard range of the ZEBRA protein is produced. (iv) After washing, 50 µl of the biotinylated AZ 130 antibody is added simultaneously at a concentration of 5 µg/ml. The plate is incubated under stirring at ambient temperature for 2 hours. After three washings, the detection is carried out with alkaline phosphatase avidin (Invitrogen) diluted to 1/500 in PBS-Tween 20 0.05%-BSA 1%. Incubation takes place for 60 minutes at ambient temperature under stirring. The wells are then washed four times with the same buffer, PBS Tween 20 0.1%. (v) Development is carried out using a chromogenic substrate, p-nitrophenylphosphate, (Sigma). Thus the pNPP is presented in the form of tablets that must be diluted in diethanolamine buffer (pH=9.5) in order to obtain a concentration of 1 mg/ml. 100 µl/well of this solution are added. The reaction must develop for 45 nm in darkness. The OD reading takes place at 405 nm (reference absorbance at 630 nm).

3—Method of Assay of the Anti-ZEBRA Antibodies

The assay of the anti-ZEBRA antibodies is carried out according to an ELISA test described by Marechal et al., 1993 Res. Virol. 144: 397-404. The recombinant ZEBRA protein originates from a strain of *Escherichia coli* transformed by the pET3c plasmid containing the coding part of the BZLF1 gene under the control of a transcription unit of the T7 polymerase type. The recombinant ZEBRA protein is used to coat the bottom of the wells of a microplate and serves for attaching the anti-ZEBRA antibodies. The anti-ZEBRA antibody titre is defined using the final point dilution method described by Vaur et al. 1986, J. Clin. Microbiol., 24: 596-599.

4—Results

The measurement of the concentration of the ZEBRA antigen as well as the titration of the anti-ZEBRA antibodies were carried out on samples of serums originating from the 14 patients of the cohort and were tested according to the techniques specified above. The results are shown in Table 1 below.

TABLE 1

Detection of the ZEBRA antigen and anti-ZEBRA antibodies in the serum of immunocompetent patients.

| Patients | ZEBRA antigen (µg/ml) | Anti-ZEBRA IgG (dilution) |
|---|---|---|
| #80 | <0.15 | 512 |
| #81 | <0.15 | 256 |
| #82 | <0.15 | 512 |
| #83 | <0.15 | 128 |
| #84 | <0.15 | 128 |
| #87 | <0.15 | 64 |
| #88 | <0.15 | 1024 |
| #89 | <0.15 | 16384 |
| #91 | <0.15 | 1024 |
| #92 | <0.15 | 64 |
| #93 | <0.15 | 128 |
| #94 | <0.15 | <64 |
| #95 | <0.15 | 256 |
| #96 | <0.15 | 256 |

The ZEBRA antigen is found at a concentration less than 0.15 µg/ml in the serum of the 14 patients tested. The presence of anti-ZEBRA antibodies is detected in titres that can vary greatly from one patient to the other. In patients #88, #89 and #91, the EBV replication phase was more active than in patients #87 and #92. It is generally acknowledged that, starting from an anti-ZEBRA antibody titre of 128, EBV is in replication phase.

These results show that the 14 immunocompetent patients presenting no PTLD of the cohort are all seropositive for the EBV virus but do not present strong replication of the virus measurable by the quantity of circulating ZEBRA antigen.

EXAMPLE 2: ASSAY OF THE CIRCULATING ZEBRA ANTIGEN, ANTI-ZEBRA ANTIBODIES AND THE EBV VIRAL LOAD IN IMMUNOSUPPRESSED PATIENTS PRESENTING NO PTLD

1—Patients

Three patients seropositive for EBV and having received a bone marrow transplant but presenting no clinical sign of lymphoproliferation were tested and the presence of the ZEBRA antigen or anti-ZEBRA antibodies as well as the measurement of the EBV viral load were assessed.

2—Method of Assay of the ZEBRA Antigen and Anti-ZEBRA Antibodies

The methods have been described precisely in Example 1 above.

3—Measurement of the EBV Viral Load 3.1—Extraction of the DNAs

Total DNA extraction is carried out using a MagNA Pure Compact Nucleic Acid Isolation kit (Roche-Applied). In brief, the mononucleated cells (PBMC) are isolated by centrifugation on Ficoll-Hypaque, density 1.077, from a sample of whole blood collected on EDTA. The PBMCs are lysed with a solution containing chaotropic salts and proteinase K and the nucleic acids are captured on the surface of magnetic beads (Glass Magnetic Particles). Successive washings make it possible to elute the non-bound substances and the DNA is eluted with a saline buffer at a low concentration.

3.2—Standard Ranges

Three standard ranges are established from a series of dilutions of plasmid constructions comprising PCR products relating to the BALF-5 or ZEBRA genes. A double-stranded DNA of 90 pb for the BALF-5 gene and 100 pb for the ZEBRA gene were each cloned in a pCR2.1 vector.

The BALF-5 and ZEBRA standard ranges extend from $10^3$ to $10^8$ copies/ml.

The slopes of the standard ranges are respectively:
- −3.47 with an intercept at 47.42 and an $R^2$ value of 0.997869 for BALF-5,
- −3.41 with an intercept at 46.62 and an $R^2$ value of 0.998847 for ZEBRA (probe of SEQ ID NO: 7), and
- −3.49 with an intercept at 47.42 and an $R^2$ value of 0.997320 for ZEBRA (probe of SEQ ID NO: 8).

These results demonstrate the perfect linearity of these two standard ranges. The PCR effectiveness is 94% for BALF-5 and 97% (probe of SEQ ID NO: 7) or 93% (probe of SEQ ID NO: 8) for ZEBRA respectively.

3.3—PCR

The pair of primers and the probe specific to the BALF-5 gene encoding the DNA polymerase of EBV have already been described in the literature (Kimura et al., J. Clin. Microbiol. 1999 January; 37(1): 132-136).

A pair of primers and a probe have been specifically designed by the inventors for ZEBRA. The sequences are given in Table 2 below:

TABLE 2

Sequences of the primers and probes used for the detection of the EBV viral load.

| | | |
|---|---|---|
| Balf-5 (F) | SEQ ID NO: 2 | 5'-CGGAAGCCCTCTGGAC TTC-3' |
| Balf-5 (R) | SEQ ID NO: 3 | 5'-CCCTGTTTATCCGATG GAATG-3' |
| Balf-5 (S) | SEQ ID NO: 4 | 5'-FAM TGTACACGCACG AGAAATGCGCC TAMRA-3' |
| ZEBRA (F) | SEQ ID NO: 5 | 5'-CCAGGCTTGGGCACAT CT-3' |
| ZEBRA (R) | SEQ ID NO: 6 | 5'-CCCATCTAAACGCCTG ATTTTT-3' |
| ZEBRA (S) | SEQ ID NO: 7 | 5'-FAM CATTTTCAGATG ATTTGGCAGCAGCCAC TAMRA-3' |
| ZEBRA (S) | SEQ ID NO: 8 | 5'-FAM CTTCAACAGGAG GCGC TAMRA-3' |

The BALF-5 reaction mix comprises 5 pmol of probe of sequence SEQ ID NO: 4, 7.5 pmol of sense primer of sequence SEQ ID NO: 2, 7.5 pmol of anti-sense primer of sequence SEQ ID NO: 3, 1× of Taq Man Universal PCR Master Mix (Applied Biosystems) and 10% of Pre-Mix Cl Simplexa diluted to 1/100.

The ZEBRA reaction mix comprises 5 pmol of probe of sequence SEQ ID NO: 7, 7.5 pmol of sense primer of sequence SEQ ID NO: 5, 7.5 pmol of anti-sense primer of sequence SEQ ID NO: 6, 1× of Taq Man Universal PCR Master Mix (Applied Biosystems) and 10% Cl Simplexa Pre-Mix diluted to 1/100.

The amplification thermal profile is:
1 cycle of 2 minutes at 50° C.,
1 cycle of 10 minutes at 95° C.,
45 cycles of [15 seconds at 95° C. then 1 minute at 60° C.].

The amplifications are carried out on an ABI Prism 7500 device (Applied Biosystems).

The size of the amplicons obtained is 90 pb for Balf-5 and 100 pb for ZEBRA respectively.

4—Results

The measurement of the concentration of the ZEBRA antigen, the titration of the anti-ZEBRA antibodies and the measurement of the EBV viral load were carried out on samples of serums originating from 3 patients were tested according to the techniques specified above. The results are shown in Table 3 below.

TABLE 3

Detection of the ZEBRA antigen, anti-ZEBRA antibodies and the EBV viral load in theserum of immunosuppressed patients not developing PTLD.

| Patients | Date | EBV viral load (copies/ml) | ZEBRA antigen (µg/ml) | Anti-ZEBRA IgG (dilution) |
|---|---|---|---|---|
| #1 = AK | Jan. 12, 2010 | | transplant | |
| | Feb. 15, 2010 | 0 | <0.15 | 1024 |
| | Apr. 23, 2011 | 925 | <0.15 | 1024 |
| #2 = BER | Sep. 23, 2009 | | transplant | |
| | Oct. 12, 2009 | 0 | <0.15 | 64 |
| | Dec. 09, 2009 | 0 | <0.15 | 512 |
| #3 = AUG | Sep. 15, 2009 | | transplant | |
| | Oct. 05, 2009 | 0 | <0.15 | 256 |
| | Dec. 28, 2009 | 7210 | <0.15 | 256 |

For patients #1 and #3, the EBV viral load, which is undetectable during the month following the transplant, reaches approximately $10^3$ to $10^4$ copies/ml one hundred days after the transplant has taken place. In parallel, the quantity of anti-ZEBRA antibodies does not vary during this time interval. Finally, the ZEBRA antigen is at a concentration less than 0.15 µg/ml, which means that EBV is not in strong replication phase. Despite increasing the viral load, it therefore appears unnecessary to treat these patients in order to prevent a lymphoma.

For patient #2, the viral load remains at zero and the ZEBRA antigen is at a concentration less than 0.15 µg/ml not only during the month following the transplant but also 77 days after the transplant has taken place. On the other hand, the patient has an anti-ZEBRA antibody titre comprised between 64 and 512 which indicates not only that the patient is seropositive for EBV but that the virus is very probably starting strong replication in the host cells.

EXAMPLE 3: ASSAY OF THE CIRCULATING ZEBRA ANTIGEN, ANTI-ZEBRA ANTIBODIES, EBV VIRAL LOAD AND IL-10 IN IMMUNOSUPPRESSED PATIENTS PRESENTING A PTLD

1—Patients

Four patients who are seropositive for EBV, having received a bone marrow transplant and for whom lymphoproliferation was diagnosed were studied. The presence of the ZEBRA antigen or anti-ZEBRA antibodies as well as the measurement of the EBV viral load and the concentration of IL-10 were assessed. A kinetic study of these biological parameters was carried out.

2—Method of Assay of the ZEBRA Antigen and Anti-ZEBRA Antibodies

The methods are described precisely in Example 1 above.

3—Measurement of the EBV Viral Load

The methods are described precisely in Example 2 above.

4—IL-10 Assay

IL-10 assay of the samples of patients is carried out using the commercial kit Human IL-10 CytoSet™ (Invitrogen, Camarillo, USA) according to a five-stage ELISA method: (i) coating of a 96-well microplate with anti-Human IL-10 antibodies at a rate of 0.1 µg/well. The microplate is incubated at 4° C. for from 12 to 18 hours. (ii) washing of the microplate then incubation of 300 µl/well of Assay Buffer solution at ambient temperature for one hour. (iii) addition of 100 µl of standard or of samples and 50 µl of detection antibodies coupled with biotin/well and incubation under stirring at ambient temperature for 2 hours. (iv) the microplate is rinsed 5 times and 100 µl of streptavidin-HRP/well is incubated under stirring at ambient temperature for 30 minutes. (v) the microplate is rinsed 5 times and 100 µl of TMB chromogenic substrate/well is incubated under stirring at ambient temperature for 30 minutes. At the end of this incubation period 100 µl of stopping solution is added to each of the wells. OD reading takes place at 450 nm during the 30 minutes following the addition of the stopping solution.

5—Results

The measurement of the concentration of the ZEBRA antigen, the titration of the anti-ZEBRA antibodies, the measurement of the EBV viral load and the IL-10 assay were carried out on samples of serums originating from the 4 patients according to the techniques specified above. The results are shown in Table 4 below.

TABLE 4

Detection of the ZEBRA antigen, anti-ZEBRA antibodies, EBV viral load and concentration of IL-10 in the serum of immunosuppressed patients developing a PTLD.

| | EBV viral load (copies/150,000 cells) | ZEBRA antigen (µg/ml) | Anti-ZEBRA IgG (dilution) | IL-10 (pg/ml) |
|---|---|---|---|---|
| | | Patient # 1 | | |
| D0 | | Transplant | | |
| D21 | 0 | <0.15 | <64 | 0 |
| D36 | $2.5 \times 10^4$ | <0.15 | <64 | 0 |

TABLE 4-continued

Detection of the ZEBRA antigen, anti-ZEBRA antibodies, EBV viral load and concentration of IL-10 in the serum of immunosuppressed patients developing a PTLD.

| | EBV viral load (copies/150,000 cells) | ZEBRA antigen (µg/ml) | Anti-ZEBRA IgG (dilution) | IL-10 (pg/ml) |
|---|---|---|---|---|
| D56 | $2.0 \times 10^6$ | 8.49 | 256 | 0 |
| D61 | $1.0 \times 10^4$ | 1.62 | 0 | 0 |
| D68 | $1.2 \times 10^4$ | <0.15 | 64 | 0 |
| D71 | $1.7 \times 10^4$ | <0.15 | <64 | 100 |
| D75 | $3.9 \times 10^4$ | <0.15 | 64 | 0 |
| D82 | $1.6 \times 10^4$ | 7.61 | 64 | 0 |
| D89 | $1.5 \times 10^3$ | <0.15 | 64 | 0 |
| D93 | $6.9 \times 10^3$ | <0.15 | 128 | 0 |
| D96 | $1.2 \times 10^3$ | <0.15 | 64 | 0 |
| D103 | $1.9 \times 10^3$ | <0.15 | 256 | 0 |
| D110 | $1.7 \times 10^3$ | 1.54 | ND | 0 |
| D124 | 0 | 8.32 | 64 | ND |
| Patient # 2 | | | | |
| D0 | | Transplant | | |
| D88 | 0 | 96.5 | 512 | 220 |
| D102 | $5.7 \times 10^3$ | 36.17 | <64 | 150 |
| D141 | $1.7 \times 10^3$ | <0.15 | <64 | 0 |
| D144 | $2.9 \times 10^3$ | <0.15 | <64 | 120 |
| D151 | $6.3 \times 10^3$ | <0.15 | 64 | 0 |
| D159 | $6.0 \times 10^5$ | <0.15 | 64 | 150 |
| Patient # 3 | | | | |
| D0 | | Transplant | | |
| D11 | $5.3 \times 10^2$ | <0.15 | 128 | 70 |
| D14 | $1.9 \times 10^3$ | <0.15 | 512 | 70 |
| D18 | $1.7 \times 10^4$ | 4.59 | <64 | 0 |
| D32 | ND | 1.71 | ND | ND |
| D39 | $7.5 \times 10^4$ | <0.15 | 256 | 0 |
| Patient # 4 | | | | |
| D0 | | Transplant | | |
| D14 | 0 | <0.15 | 128 | ND |
| D21 | ND | <0.15 | ND | ND |
| D29 | ND | <0.15 | ND | ND |
| D32 | ND | <0.15 | ND | ND |
| D35 | $1.3 \times 10^4$ | 7.48 | 1024 | ND |
| D38 | ND | <0.15 | ND | ND |
| D42 | $1.2 \times 10^4$ | <0.15 | 512 | ND |
| D63 | ND | <0.15 | ND | ND |
| D72 | ND | <0.15 | ND | ND |
| D80 | $2.1 \times 10^4$ | <0.15 | 512 | ND |
| D95 | ND | <0.15 | 256 | ND |
| D102 | $1.2 \times 10^4$ | <0.15 | 256 | ND |
| D112 | ND | 23.24 | ND | ND |
| D121 | ND | 23.65 | ND | ND |
| D135 | ND | 1.62 | ND | ND |
| D143 | ND | 3.14 | ND | ND |

Patient #1:

Three weeks after the transplant has taken place, all the biological markers tested are at their lowest.

On D36, only the EBV viral load varies in order to reach $2.5 \cdot 10^4$ copies/150,000 cells. On D56, the EBV viral load reaches $2 \cdot 10^6$ copies/150,000 cells, the ZEBRA antigen is detected at 8.49 µg/ml and the anti-ZEBRA antibody titre has increased to 256. These markers are the clinical sign of a strong EBV replication evidenced by the ZEBRA antigen peak, the rise in the anti-ZEBRA antibody level in combination with an increase in the pool of B lymphocytes infected with EBV (EBV viral load). PTLD is diagnosed on D56 and the patient is treated with Mabthera™ once a week for four weeks.

From D61 to D75, the EBV viral load, the ZEBRA antigen level and the quantity of anti-ZEBRA antibodies decrease and stabilize at values close to those found on D36. This means that the viral replication has dropped. However on D71 an IL-10 synthesis peak is observed.

On D82, the ZEBRA antigen is detected at a value of 7.61 µg/ml whilst neither the EBV viral load nor the anti-ZEBRA antibody titre have been modified with respect to D68. This increase in the ZEBRA antigen concentration indicates that there is a resumption of the strong EBV replication.

While the EBV viral load changes little between D89 and D110, the anti-ZEBRA antibody titre increases with peaks on D93 and on D103.

On D110, the concentration of the ZEBRA antigen increases to 1.54 µg/ml, a sign of a new strong replication phase of EBV. At the same time, a new episode of PTLD is diagnosed. The patient is treated with chemo- and radiotherapy before receiving a second transplant on D124. These treatments result in a drop in the anti-ZEBRA antibody titre.

Patient #2:

On D88, whilst the EBV viral load is zero, the concentration of ZEBRA antigen reaches 96.5 µg/ml, the anti-ZEBRA antibody titre is 512 and the IL-10 is at 220 pg/ml. These markers are the sign of a strong EBV replication.

On D102, the EBV viral load reaches $5.7 \cdot 10^3$ copies/150,000 cells, a sign that a greater number of B lymphocytes are infected with EBV.

On D141 and D144, although the EBV viral load remains stable, it is possible to observe not only a reduction in the anti-ZEBRA antibody titre but also a reduction in ZEBRA antigen concentration. This reflects a drop in the replicative activity of EBV. In parallel on D144, an IL-10 secretion peak is observed.

On D159, the EBV viral load increases by two logs and a new IL-10 peak is detected. PTLD is diagnosed and the patient is treated with Mabthera™.

Patient #3

Two weeks after the transplant has taken place (D14), the anti-ZEBRA antibody titre increases in order to reach 512. This reflects the start of strong EBV replication. This hypothesis is confirmed on D18 by the increase in the ZEBRA antigen level which passes from <0.15 µg/ml to 4.59 µg/ml and by the increase in the EBV viral load by one log in four days.

On D39, PTLD is diagnosed.

Patient #4

On D35, the EBV viral load reaches $1.3 \cdot 10^4$ copies/150,000 cells, the ZEBRA antigen is detected at 7.48 µg/ml and the anti-ZEBRA antibody titre has increased to 1024. These markers are the clinical sign of a strong EBV replication evidenced by the ZEBRA antigen peak, the rise in the anti-ZEBRA antibody level in combination with an increase in the pool of B lymphocytes infected with EBV (EBV viral load). PTLD is diagnosed on D35 and the patient is treated with Mabthera™ once a week for four weeks.

As from D112, the ZEBRA antigen level varies from 23 to 1.62 µg/ml, suggesting a resumption of the strong EBV replication.

The invention claimed is:

1. A method of diagnosing malignant lymphoproliferation associated with a replicative form of Epstein-Barr virus (EBV) or with a tumor associated with EBV, in a patient seropositive for EBV,
said process comprising:
provide a biological body fluid sample collected from said patient seropositive for EBV; and
conducting a sandwich ELISA on said sample to measure the amount of a soluble circulating protein complex comprising BamHI Z Epstein-Barr virus replication activator (ZEBRA) protein of sequence SEQ ID NO: 1,
wherein in said sandwich ELISA, AZ125 antibody is absorbed on a suitable plate to capture the soluble circulating protein complex, and AZ130 antibody is used for detecting the protein complex captured by the AZ125 antibody;
wherein a measured amount of said soluble circulating protein complex greater than or equal to 0.15 micrograms/ml of biological body fluid indicates said patient having said malignant lymphoproliferation.

2. The method according to claim 1, wherein the patient is an immunosuppressed patient or immunodeficient patient belonging to the group consisting of patient awaiting a transplant, patient having received a transplant, patient seropositive for an immunosuppressive virus, patient seropositive for HIV, and patient having a genetically transmitted immunological deficit.

3. The method according to claim 2, for the diagnosis of a first episode of lymphoproliferation, said first episode of lymphoproliferation occurring before initiation of any therapeutic treatment of a lymphoma.

4. The method according to claim 2, for the diagnosis of a reactivation of the replicative form of EBV occurring following a treatment of the patient for a first episode of lymphoma associated with EBV reactivation.

5. The method according to claim 2, wherein the patient is immunocompetent and does not present clinical signs of infectious mononucleosis.

6. The process according to claim 1, wherein said biological body fluid sample is blood or serum.

7. The process according to claim 1, wherein said tumor associated with EBV is nasopharyngeal cancer.

8. A method of measuring the amount of a soluble circulating protein complex comprising the BamHI Z Epstein-Barr virus replication activator (ZEBRA) protein of sequence SEQ ID NO: 1 in a biological body fluid sample, the method comprising:
providing the biological body fluid sample; and
conducting a sandwich ELISA on said sample, wherein in said sandwich ELISA, AZ125 antibody is absorbed on a suitable plate to capture the soluble circulating protein complex, and AZ130 antibody is used for detecting said protein complex captured by the AZ125 antibody.

* * * * *